United States Patent
Hall (10) Patent No.: US 10,729,139 B2
(45) Date of Patent: *Aug. 4, 2020

(54) ACID-SOLUBILIZED COPPER-AMMONIUM COMPLEXES AND COPPER-ZINC AMMONIUM COMPLEXES, COMPOSITIONS, PREPARATIONS, METHODS, AND USES

(71) Applicant: Myco Sciences Limited, Buckinghamshire (GB)

(72) Inventor: Tony John Hall, London (GB)

(73) Assignee: Myco Sciences Limited, Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/103,872

(22) PCT Filed: Dec. 12, 2014

(86) PCT No.: PCT/US2014/069908
§ 371 (c)(1),
(2) Date: Jun. 12, 2016

(87) PCT Pub. No.: WO2015/089358
PCT Pub. Date: Jun. 18, 2015

(65) Prior Publication Data
US 2016/0309722 A1  Oct. 27, 2016

Related U.S. Application Data

(63) Continuation of application No. 14/106,676, filed on Dec. 13, 2013, now Pat. No. 9,474,282.

(51) Int. Cl.
| | |
|---|---|
| A01N 59/20 | (2006.01) |
| A61K 33/34 | (2006.01) |
| A61Q 19/00 | (2006.01) |
| C02F 1/50 | (2006.01) |
| A01N 59/16 | (2006.01) |
| A61K 9/00 | (2006.01) |
| A61K 33/02 | (2006.01) |
| A61K 33/30 | (2006.01) |
| A61K 47/02 | (2006.01) |
| A61K 47/12 | (2006.01) |
| A61K 9/06 | (2006.01) |
| A61K 47/36 | (2006.01) |
| A61K 8/04 | (2006.01) |
| A61K 8/19 | (2006.01) |
| A61K 8/27 | (2006.01) |
| C02F 103/42 | (2006.01) |

(52) U.S. Cl.
CPC ............ *A01N 59/20* (2013.01); *A01N 59/16* (2013.01); *A61K 8/042* (2013.01); *A61K 8/19* (2013.01); *A61K 8/27* (2013.01); *A61K 9/0014* (2013.01); *A61K 9/06* (2013.01); *A61K 33/02* (2013.01); *A61K 33/30* (2013.01); *A61K 33/34* (2013.01); *A61K 47/02* (2013.01); *A61K 47/12* (2013.01); *A61K 47/36* (2013.01); *A61Q 19/00* (2013.01); *C02F 1/50* (2013.01); *C02F 2103/42* (2013.01)

(58) Field of Classification Search
None
See application file for complete search history.

(56) References Cited

U.S. PATENT DOCUMENTS

| | | |
|---|---|---|
| 1,988,752 A | 1/1935 | Sessions |
| 2,414,660 A | 1/1947 | Nikitin |
| 2,540,209 A | 2/1951 | Nikitin |
| 4,048,324 A | 9/1977 | Kohn |
| 4,075,324 A | 2/1978 | Thizy |
| 4,193,993 A | 3/1980 | Hilditch |
| 4,544,666 A | 10/1985 | Thirumalachar |
| 4,622,248 A | 11/1986 | Leach |
| 4,675,431 A | 6/1987 | Privitizer |
| 4,952,398 A | 8/1990 | Tapin |
| 5,373,025 A | 12/1994 | Gay |

(Continued)

FOREIGN PATENT DOCUMENTS

| | | |
|---|---|---|
| CN | 1076080 A | 9/1993 |
| CN | 1826899 A1 | 9/2006 |

(Continued)

OTHER PUBLICATIONS

Brunings et al., "Are Phosphorous and Phosphoric Acids Equal Phosphorous sources for Plant Growth?" University of Florida Institute of Food and Agricultural Sciences. Original publication date Apr. 2005. Revised Mar. 2012, Jan. 2015. Obtained on Oct. 15, 2015 at https://edis.ifas.ufl.edu/pdffiles/HS/HS25400.pdf. EFS file name: 20170322_15-103872_IDS2_NPL_Cite1.pdf.

(Continued)

*Primary Examiner* — Celeste A Roney (74) *Attorney, Agent, or Firm* — John M. Hammond; Patent Innovations LLC (57) ABSTRACT

An antimicrobial composition is disclosed that contains an acid-solubilized copper ammonium or copper-zinc ammonium complex that is effective against microorganisms such as nosocomial or environmental bacteria, fungi, viruses, and the like. The antimicrobial composition can be used in the preparation of a medicament for treating microbes or a microbial infection, and may contain a carrier to create a cream, soap, wash, spray, dressing, cleanser, cosmetic product, topical drug product, or other antimicrobial product.

19 Claims, 5 Drawing Sheets

(56) References Cited

U.S. PATENT DOCUMENTS

| | | | |
|---|---|---|---|
| 5,736,164 | A | 4/1998 | Taylor |
| 6,168,643 | B1 | 1/2001 | Hsu |
| 6,340,384 | B1 | 1/2002 | Walker |
| 6,896,908 | B2 | 5/2005 | Lloyd et al. |
| 6,942,878 | B2 | 9/2005 | Ishii et al. |
| 7,060,302 | B1 | 6/2006 | Hickok |
| 8,012,511 | B1 | 9/2011 | Cummins et al. |
| 8,067,403 | B2 | 11/2011 | Whiteford et al. |
| 8,206,732 | B2 | 6/2012 | Nelson |
| 8,221,796 | B2 | 7/2012 | Martinez |
| 8,273,791 | B2 | 9/2012 | Ramirez et al. |
| 8,287,893 | B2 | 10/2012 | Crudden |
| 8,293,282 | B2 | 10/2012 | Patel |
| 8,491,812 | B2 | 7/2013 | Moore |
| 9,474,282 | B2 * | 10/2016 | Hall .................. A01N 59/20 |
| 2002/0193351 | A1 | 12/2002 | Taylor |
| 2004/0001791 | A1 | 1/2004 | Zeller |
| 2004/0258838 | A1 | 12/2004 | Richardson |
| 2006/0089342 | A1 | 4/2006 | Gavin et al. |
| 2006/0159772 | A1 | 7/2006 | Garavaglia |
| 2007/0275101 | A1 | 11/2007 | Lu et al. |
| 2008/0004177 | A1 | 1/2008 | Pfeiffer et al. |
| 2008/0166424 | A1 | 7/2008 | Mixon |
| 2009/0226494 | A1 | 9/2009 | Hickok |
| 2010/0015245 | A1 | 1/2010 | Harrison et al. |
| 2012/0021911 | A1 | 1/2012 | Majure et al. |
| 2013/0309517 | A1 | 11/2013 | Pallaske |
| 2014/0213544 | A1 | 7/2014 | Majure |
| 2015/0119361 | A1 | 4/2015 | Schutz et al. |
| 2015/0164085 | A1 * | 6/2015 | Hall .................. A01N 59/20 424/638 |
| 2016/0192643 | A1 | 7/2016 | Stark |

FOREIGN PATENT DOCUMENTS

| | | |
|---|---|---|
| DE | 2807293 A1 | 8/1979 |
| EP | 0136137 A2 | 4/1984 |
| EP | 0125137 A2 | 11/1984 |
| EP | 0136137 A1 | 4/1985 |
| EP | 0136173 A2 | 4/1985 |
| EP | 2286666 A1 | 2/2011 |
| FR | 1544172 A1 | 9/1968 |
| GB | 1119058 A1 | 7/1968 |
| GB | 2077740 A1 | 12/1981 |
| JP | 01305013 A1 | 12/1989 |
| JP | H0680527 A | 3/1994 |
| JP | 2013231001 A | 11/2013 |
| JP | 2013231001 A1 | 11/2013 |
| WO | 8504668 A1 | 10/1985 |
| WO | 91/13552 A1 | 9/1991 |
| WO | 02060248 A2 | 8/2002 |
| WO | 02096202 A1 | 12/2002 |
| WO | 2006128677 A2 | 12/2006 |
| WO | 2007017220 A2 | 2/2007 |
| WO | 2007045256 A1 | 4/2007 |
| WO | 2008035079 A2 | 3/2008 |
| WO | 2009055799 A2 | 4/2009 |
| WO | 2009082206 A1 | 7/2009 |

OTHER PUBLICATIONS

Written Opinion in PCT Application No. IB2015/001259, dated Oct. 19, 2015. EFS file name: 20170322_15-103872_IDS2_NPL_Cite2.pdf.

ChemDemos (2012), Copper-Ammonia Complex, pp. 1-3. EFS file name: 20170322_15-103872_IDS1_NPL_Cite1.

Labnet Internatinoal, Inc. (2010), Instruction Manual, pp. 1-12. EFS file name: 20170322_15-103872_IDS1_NPL_Cite2.

Hall et al., Biocides for laundry decontamination, Focus on Detergency, Feb. 2010, pp. 8-10, vol./issue NA, Household and Personal Care Today. United Kingdom. EFS file name 20170322_15-103872_IDS1_NPL_Cite3.

Hamilton et al., Performance of ultramicrofibre cleaning technology with or without addition of a novel copper-based biocide, Journal of Hospital Infection, Oct. 12, 2009 . . . pp. 62-71, vol. 74, Elsevier, published on-line. EFS file name 20170322_15-103872_IDS1_NPL_Cite4.

Hall et al, Decontamination of laundry at low temperature with CuWB50, a novel copper-based biocidal compound, American Journal of Infection Control, Aug. 2009, pp. 478-483 . . . vol. 37, No. 6, the Association for Professionals in Infection Control and Epiemiology, Inc., published on-line. EFS file name 20170322_15-103872_IDS1_NPL_Cite5.

Gant, Novel copper-based biocides: efficacy against multiresistant Acinetobacter in an ICU environment, published online Aug. 3, 2007. EFS file name 20170322_15-103872_IDS1_NPL_Cite6.

Gant et al.,Three novel highly charged copper-based biocides:safety and efficacy against healthcare-associated organisms,Journal of Antimicrobial Chemotherapy,Jun. 13, 2007 . . . pp. 294-299, vol. 60, Oxford University Press. EFS file name 20170322_15-103872_IDS1_NPL_Cite7.

Hall et al.,A comparison of the antibacterial efficacy and cytotoxicity to cultured human skin cells of 7 commercial hand rubs and Xgel,a new copper-based biocidal hand rub . . . The American Journal of Infection Control, 2009, pp. 322-326, vol. 37, No. 4, the Association for Professionals in Infection Control and Epidemiology, Inc. Published on-line. EFS file name 20170322_15-103872_IDS1_NPL_Cite8.

Hall et al., A UK district general hospital cleaning study: a comparison of the performance of ultramicrofibre technology with or without addition of a novel copper-based . . . biocide with standard hypochlorite-based cleaning, Journal of Infection Prevention, Nov. 2011, pp. 232-236, vol. 12, No. 6, Sage Publishing, U.K. EFS file name 20170322_15-103872_IDS1_NPL_Cite9.

Gant et al., Letters to the Editor, The Hospital Infection Society, Nov. 14, 2009, pp. 82-84, vol. issue unknown, Elsevier, published on-line. EFS file name 20170322_15-103872_IDS1_NPL_Cite10.

Moore et al., The efficacy of the inorganic copper-based biocide CuWB50 is compromised by hard water, Letters in Applied Microbiology, Feb. 28, 2008, pp. 655-660, vol. 46, . . . The Society for Applied Microbiology, Published on-line. EFS file name 20170322_15-103872_IDS1_NPL_Cite11.

Hall et al., Effect of the dried residues of two hand gels on the survival of meticillin-resistant *Staphylococcus aureus* and *Acinetobacter calcoaceticus-baumannii*, . . . Journal of Infection Prevention, May 2010, pp. 70-73, vol. 2, No. 3, Sage Publications, Published on-line. EFS file name 20170322_15-103872_IDS1_NPL_Cite12.

Hall et al., A hospital cleaning study using microfibre and a novel copper biocide. I. Microbiological studies, Journal of Infection Prevention, Sep. 2011, pp. 188-194, . . . vol. 12, No. 5, Sage Publications, Published on-line. EFS file name 20170322_15-103872_IDS1_NPL_Cite13.

Wren et al., Removing bacteria from hospital surfaces:a laboratory comparision of ultramicrofibre and standard cloths, Journal of Hospital Infection, Sep. 17, 2008, vol. 70 . . . pp. 265-271, Elsevier Ltd., Published on-line. EFS file name 20170322_15-103872_IDS1_NPL_Cite14.

"Copper oxychloride fungicide and its effect on growth and oxidative stress of potato plants," Ferreira et al., Pesticide Biochemistry and Physiology, vol. 112, Jun. 2014, pp. 63-69, May 8, 2014. 20190113_15-103872_IDS_NPL_Cite1.

"Effect of postinfection application of phosphorous (phosphonic) acid on the incidence and sporulation of Plasmopara viticola on grapevine," Wick et al., Faculty of Engineering and Information Sciences—Papers: Part A, University of Wollongong Australia, 1991. EFS file name: 20190113_15-103872_IDS_NPL_Cite2.

"A Progress Report on the Effect of Zinc as a Constituent of Potato Fiungicides," Callbeck, L. C., American Potato Journal, vol. 31, pp. 341-348, Apr. 20, 1954. EFS file name: 20190113_15-103872_IDS_NPL_Cite3.

"Ultrastructure and Development of Sclerotia of Botrytis cinerea Pers. in vitro," Nair et al., Journal of Phytopathology, vol. 119, Issuel, May 1987. EFS file name: 20190113_15-103872_IDS_NPL_Cite4.

(56) References Cited

OTHER PUBLICATIONS

Nufarm Oxydul(R) DF Fungicide product information, Dec 4, 2009.
EFS file name: 20190113_15-103872_IDS_NPL_Cite5.

* cited by examiner

ACID-SOLUBILIZED COPPER-AMMONIUM COMPLEXES AND COPPER-ZINC AMMONIUM COMPLEXES, COMPOSITIONS, PREPARATIONS, METHODS, AND USES

TECHNICAL FIELD

This invention relates generally to compositions with antimicrobial activity, and more specifically to compositions containing acid-solubilized copper-ammonium or acid-solubilized copper-zinc-ammonium complexes as active ingredients.

BACKGROUND ART

The antimicrobial effects of copper metal and copper salts have been known since ancient times. The role of copper as an anti-microbial agent was first described in the Smith Papyrus, an Egyptian medical text written around 2,600 BC, which describes the application of copper to sterilize chest wounds and drinking water.

The Greeks, Romans and Aztecs used copper metal or its compounds for the treatment of chronic infections and for hygiene in general. For example, in the Hippocratic Collection copper is recommended for the treatment of leg ulcers associated with varicose veins. To prevent infection of fresh wounds, the Greeks sprinkled a dry powder composed of copper oxide and copper sulfate on the wound. Another antiseptic wound treatment at the time was a boiled mixture of honey and red copper oxide. The Greeks had easy access to copper since the metal was readily available on the island of Kypros (Cyprus) from which the Latin name for copper, cuprum, is derived.

The Ancient Indian ayurvedic text Charaka Samhita (300 BC) also mentions how copper kills fatal microbes, including its role in the purification of drinking water. Pliny (23 to 79 A.D.) described a number of remedies involving copper, for example, black copper oxide was given with honey to remove intestinal worms.

In more modern times, the first observation of copper's role in the immune system was published in 1867 when it was reported that, during the cholera epidemics in Paris of 1832, 1849 and 1852, copper workers were immune to the disease. Further, animals deficient in copper have been shown to have increased susceptibility to bacterial pathogens such as *Salmonella* and *Listeria*.

Copper sulfate is the key active component of the fungicidal "Bordeaux mixture" that was invented in the 19th century and is still used in agriculture today, as are numerous other copper-based agrochemicals.

Pathogenic microbes such as bacteria, fungi and viruses are responsible for many of the diseases in multicellular organisms as illustrated by the following non-limiting examples.

In the pharmaceutical area, bacterial infections are involved in skin diseases such as acne (*Propionibacterium acnes*) and eczema (*Staphylococcus aureus*). Healthcare-acquired infections (HAIs) caused by meticillin-resistant *Staphylococcus aureus* (MRSA), *Acinetobacter* sp., *Klebsiella pneumonia* (in which the NDM-1 enzyme gene was originally identified) and *Legionella pneumophila* which is the cause of Legionnaire's disease. *Escherichia coli* (*E. coli*) is a common cause of urinary tract infections. These and other HAIs are estimated to cause the death of nearly 100,000 people in the USA annually. Pathogenic *E. coli* O157:H7 causes gastroenteritis when ingested through contaminated food. Diseases caused by fungi may be relatively mild such as athlete's foot (*Tricophyton* sp.), dandruff (*Malassezia globosa*) and thrush (*Candida albicans*), but fungi such as *Aspergillus fumigatus* (*A. fumigatus*) and *Candida albicans* (*C. albicans*), and yeasts such as *Cryptococcus neoformans* may cause life-threatening infections in immune compromised patients. Viruses are also responsible for common diseases such as colds (Rhinoviruses) and influenza (Influenza viruses A, B and C) and cold sores (Herpes simplex virus), to more serious viral diseases such as rabies and ebola.

Bacterial infections of skin wounds such as pressure sores and diabetic leg ulcers can exacerbate the condition and copper salts and copper-based compositions have been shown to be effective against these diseases by virtue of both their anti-bacterial effects and their ability to stimulate wound healing, by enhancing growth factor production.

In the cosmetic area, copper or copper-zinc compositions have been shown to be effective at, for example, ameliorating the effects of mild to moderate sunburn and mild burns, and also in reducing the itching and inflammation caused by insect bites and reducing the appearance of wrinkles.

In the agricultural area, fungal diseases are currently killing tanoaks in the western United States (*Phytophthora ramorum*) and ash trees in Europe (*Chalara fraxinea*). Fungal and bacterial diseases of grape vines, fruit and vegetable bearing plants and cereal crops are a threat to world food production.

The presence of increasing numbers of drug-resistant strains of pathogenic microbes in hospitals and in the general environment is becoming a great concern as illustrated by the following examples. Antibiotic-resistant and multi-drug resistant strains of pathogenic bacteria such as MRSA, vancomycin-resistant *Staphylococcus aureus* (VRSA). *Acinetobacter baumannii*, *E. coli* and *Mycobacterium tuberculosis* are now commonplace. Resistant strains of pathogenic fungi such as ketoconazole-resistant *C. albicans* and *A. fumigatus* are an increasing problem particularly in immune-compromised patients. Fungicide-resistant plant pathogenic fungi constantly evolve and require new anti-fungal agents for their treatment. For example, *Phytophthora infestans*, the cause of potato blight, became highly resistant to Metalaxyl in the late $20^{th}$ century. Pathogenic viruses similarly develop resistance to anti-viral drugs, the development of resistance of the H1N1 "swine flu" influenza A strain to oseltamivir phosphate (TAMIFLU®, a registered trademark of Genentech, San Francisco, Calif., USA) in the past five years being a recent example.

DISCLOSURE OF THE INVENTION

In accordance with the present invention, there is provided an antimicrobial composition comprising a solution comprising a copper salt in water; a basic ammonium salt added to the copper salt solution to generate an insoluble copper-ammonium complex; and at least one water soluble acid added to the copper salt solution to solubilize the copper-ammonium complex and to control the pit of the clear blue acid-solubilized copper-ammonium solution thus formed.

The foregoing paragraph has been provided by way of introduction, and is not intended to limit the scope of the invention as described in this specification, claims and the attached drawings.

BRIEF DESCRIPTION OF THE DRAWINGS

The invention will be described by reference to the following drawings, which like numerals refer-to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as edited by this specification, claims and the attached drawings.

BEST MODE FOR CARRYING OUT THE INVENTION

The present invention will be described by way of example, and not limitation. Modifications, improvements and additions to the invention described herein may be determined after reading this specification and viewing the accompanying drawings: such modifications, improvements, and additions being considered included in the spirit and broad scope of the present invention and its various embodiments described or envisioned herein.

The inventor has surprisingly found that acid-solubilized copper-ammonium and copper-zinc-ammonium complexes described herein are useful in combating specific pathogenic microbes that are antibiotic-resistant in the case of certain bacteria or otherwise difficult to treat or control in the case of certain bacterial and fungal strains. Furthermore, the inventor has surprisingly found that these acid-solubilized copper-ammonium complexes can be highly effective against difficult to treat bacteria, for example, MRSA and *Acinetobacter baumannii* with simultaneous lack of toxicity to human skin cells in culture at similar concentrations.

Owing to the relatively low amounts of copper that can be safely ingested (no more than 6 milligrams per day in adult humans) or tolerated by plants and animals in the environment, and particularly in the aqueous environment, the applications of the acid-solubilized copper-ammonium or copper-zinc-ammonium compositions described herein are primarily for topical use, for example, on the skins or mucous membranes of animals and humans, on the leaves of plants, or, for example, on surfaces in the environment, such as in homes or hospitals.

Exceptions to topical uses include, for example, (i) the treatment of water contaminated by one or more microbes that could be made potable by the use of an acid-solubilized copper-ammonium or acid-solubilized copper-zinc-ammonium composition to remove or kill microbes, or (ii) making water fit for use by removal or killing of microalgae or bacteria contaminating the water in a structure such as a swimming pool or hot tub by the addition of one or more of the acid-solubilized copper or copper-zinc compositions described herein.

The acid-solubilized copper-ammonium complex compositions described herein can be applied topically to the skin of a patient for preventing or treating, for example an MRSA infection or a fungal infection such as *C. albicans*. They can also be applied topically by spraying, for example, to the leaves of plants with a fungal infection such as powdery mildew. Once on the surface, the disinfecting properties of the copper ion complex can remain effective for a considerable period of time.

The acid-solubilized copper-ammonium complexes can also be applied to surfaces, for example, either by spraying or by application with a cloth, and unexpectedly can be effective against multiple different pathogenic microbes simultaneously and can provide protection against infection and re-infection with such microbes. Once on the surface, the disinfecting properties of the copper ion complex can remain effective for a considerable time.

The present acid-solubilized copper-ammonium complexes and substrates impregnated therewith can provide a very effective inhibition of the growth of pathogenic microbes hitherto difficult to treat with conventional drugs and/or conventional disinfectant regimes. This inhibition of growth of pathogenic microbes can surprisingly be at concentrations that are not toxic to human skin cells.

The acid-solubilized copper-ammonium compositions can be made into topical formulations such as creams, gels, spray solutions, irrigation solutions and impregnated dressings which can be for application to skin and mucosal surfaces, leaves of plants, and work surfaces in homes, hospitals, factories, vehicles etc.

The acid-solubilized copper-ammonium and copper-zinc-ammonium compositions are conveniently prepared according to the general procedure outlined below. These disclosed embodiments of the present invention exemplify certain preferred compositions; however, these examples are not intended to limit the scope of the invention. As will be obvious to those skilled in the art, multiple variations and modifications may be made without departing from the spirit and broad scope of the present invention.

The following example describes the general protocol for making acid-solubilized copper-ammonium complex formulation Cu#3. All chemicals were obtained from Sigma-Aldrich Company Ltd., The old Brickyard, New Road, Gillingham, Dorset SP8 4XT, UK, or Oxoid Ltd., Wade Road, Basingstoke, Hampshire RG24 8PW, UK.

16.0 grams of copper sulfate pentahydrate was added to 80 milliliters of distilled water in as glass beaker using a magnetic stirrer and a stir bar with vigorous mixing to form a clear blue solution. 4 grams of ammonium carbonate was added to the copper sulfate solution in 0.5-1 gram amounts owing to the vigorous evolution of carbon dioxide which was allowed to subside between additions of the aliquots of ammonium carbonate. A pale blue insoluble copper-ammonium complex was formed during the addition of the ammonium carbonate to the copper sulfate solution and this was kept in suspension with vigorous stirring. 10.0 milliliters of phosphoric acid (85% solution) was gradually added with the evolution of carbon dioxide and the solubilization of the copper-ammonium complex. Sufficient acid must be added so as to completely solubilize the copper-ammonium complex and to control the pH of the solution. The resulting clear, brilliant blue solution was vigorously stirred for a further 5 minutes and then made up to a final volume of 100 milliliters with distilled water.

It is preferred that the elemental concentration of copper in the compositions is of the order 1 to 10 grams/deciliter preferably 3 to 7 grams/deciliter, more preferably 3.5 to 5 grams/deciliter, with the solvent phase being distilled or deionised water.

For examples of other acid-solubilized copper-ammonium complex formulations based on this protocol see Table 1 below. In the Table, gram or grams is abbreviated with the letter g and milliliter or milliliters being abbreviated with the letters ml.

TABLE 1

Examples of acid solubilized copper-ammonium complex compositions (Cu#)

Ingredients added per deciliter of distilled water

| Composition | CuSO$_4$•5H$_2$O | (NH$_4$)$_2$CO$_3$ | Acid |
|---|---|---|---|
| Cu#1 | 16.0 g* | 2.0 g | 5.0 g H$_3$PO$_4$ (85%) |
| Cu#3 | 16.0 g | 4.0 g | 10.0 g H$_3$PO$_4$ (85%) |
| Cu#3a | 16.0 g | NH$_4$OH (10% solution) 3.2 ml | 2.0 g H$_3$PO$_4$ (85%) |
| Cu#9 | 16.0 g | 2.0 g | 2.3 ml HCl (~18M) |
| Cu#10 | 16.0 g | 2.0 g | 1.5 ml Glacial acetic acid |
| Cu#10a | 16.0 g | NH$_4$OH (10% solution) 1.6 ml | 1.5 ml Glacial acetic acid |
| Cu#11a | 16.0 g | NH$_4$OH (10% solution) 1.6 ml | 1.5 g Citric acid |
| Cu#12 | 16.0 g | 1.5 g | 1.0 ml H$_2$SO$_4$ (37%) |
| Cu#13 | CuCl$_2$•2H$_2$O 10.7 g* | 3.0 g | 2 ml H$_2$SO$_4$ (37%) |
| Cu#16 | 15.0 g** | NH$_4$HCO$_3$ 6.0 g | 8.0 g H$_3$PO$_3$ |
| Cu#27 | 15.0 | NH$_4$OH (10% solution) 2.0 ml | 2.4 g H$_3$PO$_3$ |

*The indicated amounts produce a stock solution of approximately 4.0 grams/deciliter or
**3.75 grams/deciliter of elemental copper.

The following example describes the general protocol for making acid-solubilized copper-zinc-ammonium formulation Cu—Zn#10.

6.0 grams of copper sulfate pentahydrate was added to 80 milliliters of distilled water in a glass beaker using a magnetic stirrer and a stir bar with vigorous mixing to form a clear blue solution. 6.6 grams of zinc sulfate heptahydrate was added to the copper sulfate solution and stirred until dissolved. 2.0 milliliters of ammonium hydroxide (10% solution) was added to the copper sulfate/zinc sulfate solution dropwise. A pale blue insoluble copper-zinc-ammonium complex was formed during the addition of the ammonium hydroxide solution to the copper sulfate/zinc sulfate solution and this was kept in suspension with vigorous stirring. 4.0 grams of phosphorous acid was gradually added in approximately 0.5 g aliquots to solubilize the copper-zinc-ammonium complex. Sufficient acid must be added so as to completely solubilize the copper-zinc-ammonium complex and to control the pH of the solution. The resulting clear, pale blue solution was vigorously stirred for a further 5 minutes and then made up to a final volume of 100 milliliters with distilled water.

It is preferred that the elemental concentration of copper and zinc in the compositions is of the order 1:1 with the solvent phase being distilled or deionised water.

For other acid-solubilized copper-zinc-ammonium formulations based on this protocol see Table 2. In the Table, gram or grams is abbreviated with the letter g and millilitres is abbreviated as ml. Referring to the exemplary compositions in Table 1 and Table 2, it can be seen that ranges of concentrations of the constituents of the compositions may vary. In certain embodiments, a composition may be prepared by adding 20-32 milliliters/liter of an ammonium hydroxide solution. In Table 2, Example Composition Cu—Zn#10, 2.0 ml NH$_4$OH solution is added, and made up to 100 ml final volume with distilled water, resulting in 20 milliliters/liter of an ammonium hydroxide solution. In Table 1, Example Composition Cu#3a, 3.2 ml NH$_4$OH solution added, and made up to 100 ml final volume with distilled water, resulting in 32 milliliters/liter of an ammonium hydroxide solution. In certain embodiments, a composition may be prepared with a concentration of elemental copper between 15 and 40 grams/liter. In Table 2, Example Compositions Cu—Zn#1, #2, #3, #7, and #10, 6.0 g copper sulfate pentahydrate is made up to 100 ml final volume with distilled water, resulting in 15 g/liter elemental copper. In Table 1, Example Compositions Cu#1 Cu#12, 16.0 g copper sulfate pentahydrate is made up to 100 ml final volume with distilled water, resulting in 40 g/liter elemental copper. In certain embodiments, a composition may be prepared with an amount of phosphorous acid of 24-50 grams/liter." In Table 1, Example Composition Cu#27, 2.4 g H$_3$PO$_3$ is added and made up to 100 ml final volume with distilled water, resulting in a phosphorous acid concentration of 50 grams/liter. In Table 2, Example Composition Cu—Zn#10, 5.0 g H$_3$PO$_3$ is added and made up to 100 ml final volume with distilled water, resulting in a phosphorous acid concentration of 50 grams/liter. In certain embodiments, a composition may be prepared with an amount of phosphoric acid is 17-85 grams/liter." In Table 1, Example Composition Cu#3a, 2.0 g H$_3$PO$_4$ (85%) H$_3$PO$_4$ is added, and made up to 100 ml final volume with distilled water, resulting in a phosphoric acid concentration of 17 grams/liter. In Table 1, Example Composition Cu#3, 10.0 g H$_3$PO$_4$ (85%) H$_3$PO$_4$ is added, and made up to 100 ml final volume with distilled water, resulting in a phosphoric acid concentration of 85 grams/liter. In certain embodiments, a composition may be prepared with a concentration of elemental zinc of 2.5-15 grams/liter. In Table 2, Example Compositions Cu—Cu—Zn#3, 1.1 g zinc sulfate heptahydrate is made up to 100 ml final volume with distilled water, resulting in 2.5 g/liter elemental zinc. In Table 2, Example Compositions Cu—Zn#1, #4-#10, 6.6 g zinc sulfate heptahydrate is made up to 100 ml final volume with distilled water, resulting in 15 g/liter elemental zinc. As will be described subsequently herein using certain EXAMPLES, the compositions may be diluted with water at a ratio of 1:100, resulting in compositions with the following concentration ranges: concentration of elemental copper between 0.15 and 0.40 grams/liter; concentration of elemental zinc between 0.25-0.15 grams/liter; amount of phosphorous acid between 0.24 and 0.50 grams/liter; and amount of phosphoric acid between 0.17 and 0.85 grams/liter.

TABLE 2

Example of acid-solubilized copper-zinc compositions (Cu—Zn#)

| Composition | Ingredients added per dL of distilled water | | | |
|---|---|---|---|---|
| | $CuSO_4 \cdot 5H_2O$ | $ZnSO_4 \cdot 7H_2O$ | $(NH_4)_2CO_3$ | Acid |
| Cu—Zn#1 | 6.0 g* | 6.6 g* | 2.0 g | 3.0 ml HCl (~18M) |
| Cu—Zn#2 | 6.0 g | 2.2 g | 2.0 g | 3.0 ml HCl (~18M) |
| Cu—Zn#3 | 6.0 g | 1.1 g | 2.0 g | 3.0 ml HCl (~18M) |
| Cu—Zn#4 | 2.0 g | 6.6 g | 2.0 g | 3.0 ml HCl (~18M) |
| Cu—Zn#5 | 1.0 g | 6.6 g | 2.0 g | 3.0 ml HCl (~18M) |
| Cu—Zn#7 | 6.0 g | 6.6 g | 2.0 g | 5.0 g $H_3PO_3$ |
| Cu—Zn#10 | 6.0 g | 6.6 g | $NH_4OH$ (10% solution) 2.0 ml | 5.0 g $H_3PO_3$ |

*The indicated amounts produce a stock solution of approximately 1.5 grams/deciliter of both elemental copper and elemental zinc.

Methods for making Aloe vera-based gel of the present invention are described herein, with examples provided.

Example 1

Sprinkle 1.0 gram of xanthan gum onto 150 milliliters of distilled water at around 60° C. in a 300 milliliter borosilicate glass beaker and mix vigorously with a whisk for 30 seconds to form a smooth, bubbly solution. Sprinkle 1.0 gram of Aloe vera powder onto the xanthan gum solution and whisk vigorously again for 30 seconds or until the Aloe vera powder is fully dissolved into the solution. Add room temperature distilled water to a final volume of 200 milliliters. Store the gel at 4° C. and use within one month. This gel was used for diluting the copper and copper/zinc compositions in the agar plate antibacterial tests. If the gel is to be used for cosmetic purposes and/or storage at room temperature then antimicrobial preservatives must be added. These may include, for example, mandelic acid, glycerol, potassium sorbate, phenoxyethanol, sodium benzoate. An effective combination is potassium sorbate (KS) and sodium benzoate (NaB). Separate stock solutions of 10.0% weight/volume of KS and NaB were prepared and 2.0 milliliters of each product was added to the xanthan gum-Aloe vera solution described above with vigorous mixing and then room temperature distilled water was added to a final volume of 200 milliliters. Acid-solubilized copper-ammonium or copper-zinc-ammonium complex compositions were diluted, for example, 1:100 vol/vol into this gel.

Example 2

In a weighed beaker gradually mix 3.0 grams of xanthan gum in ~1 gram aliquots into 3 grams of glycerol at room temperature (around 20° C.) until a smooth homogenous paste is formed. Re-weigh the beaker and its contents. Gradually add 5 grams of the glycerol-xanthan gum mixture (1 gram of the mixture should remain in the beaker) to 400 milliliters of distilled water at around 60° C. in a 800 milliliter borosilicate glass beaker whilst vigorously whisking until a clear, bubbly solution is formed. Sprinkle 2.5 grams of Aloe vera powder onto the solution and continue whisking until the Aloe vera powder is fully dissolved into the solution. Antimicrobial preservatives (e.g. 5.0 milliliters of the 10% stock solutions of KS and NaB as described above) can be added at this stage with whisking before adding room temperature distilled water to a final volume of 500 milliliters.

In order that the present invention may be illustrated, more easily appreciated and readily carried into effect by those skilled in the art, embodiments thereof will now be presented by way of non-limiting examples only and described with reference to the accompanying drawings.

Example 1. Agar Plate Test for the Antibacterial Effect of Selected Compositions on Bacteria The *Staphylococcus aureus* strain (S1) isolated from the skin of an eczema patient was cultured on tryptone-soya agar (TSA) and a single colony was cultured in RPMI-1640 medium at 37° C. overnight. The S1 (*S. aureus*) culture was diluted 1:10 with fresh RPMI-1640 medium and 0.2 milliliter was spread onto a 9 centimeter Petri dish containing TSA and allowed to dry. The *Propionibacterium acnes* strain ATCC 11828 (*P. acnes*) was cultured in brain-heart infusion broth with 1% glucose (BHI) at 37° C. for 72 hours under anaerobic conditions using an AnaeroGen sachet. A 0.2 milliliter sample of the *P. acnes* culture was spread onto a 9 centimeter Petri dish containing BHI agar and allowed to dry.

The composition to be tested was either diluted with distilled water and 5 microliters was placed onto a 5 millimeter filter paper disc or was added to the Aloe vera-based gel (without preservatives) described above at various concentrations and a 5 microliter drop was placed onto the agar surface. The plates were then incubated at 37° C. for 24 hours (under anaerobic conditions for *P. acnes*), when the zones of inhibition (ZoI) were measured (in millimeters) twice at a 90° angle using a ruler and the average diameter (D) was calculated. The area of inhibition in $mm^2$ (AoI) was calculated using the formula: $AoI=\pi \times (D/2)^2$.

Figure 1:
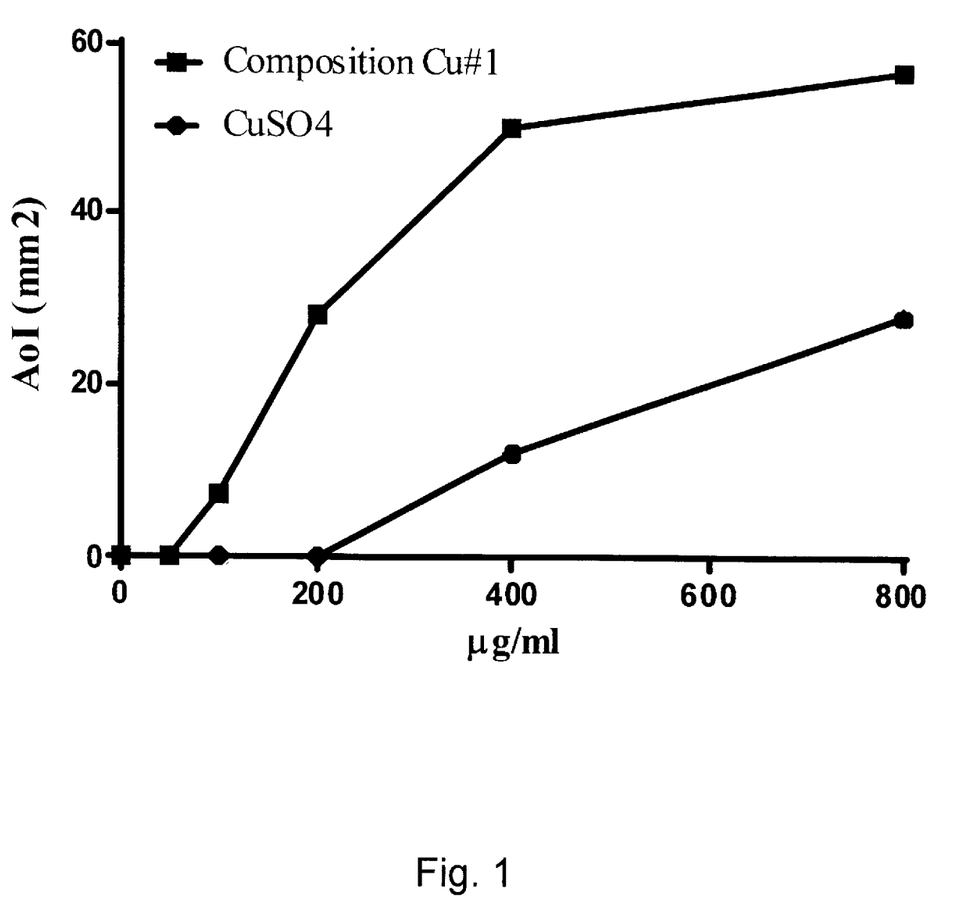
FIG. 1 is a graph depicting the effects of copper sulfate and composition Cu#1 on the growth of bacterial strain S1 (*S. aureus*)

Results:

1. The results in FIG. 1 compare the effects of copper sulfate and composition Cu#1 dissolved in gel on the growth of bacterial strain S1 (*S. aureus*) on TSA. It is clear that composition Cu#1 is approximately 4-fold more potent than copper sulfate at inhibiting the growth of S1 (*S. aureus*), since copper sulfate at 800 micrograms/milliliter and composition Cu#1 at 200 micrograms/milliliter have the same AoI (28 $mm^2$). The results show that compositions of acid-solubilized copper-ammonium complexes are surprisingly more antimicrobial than copper sulfate alone.

Figure 2:
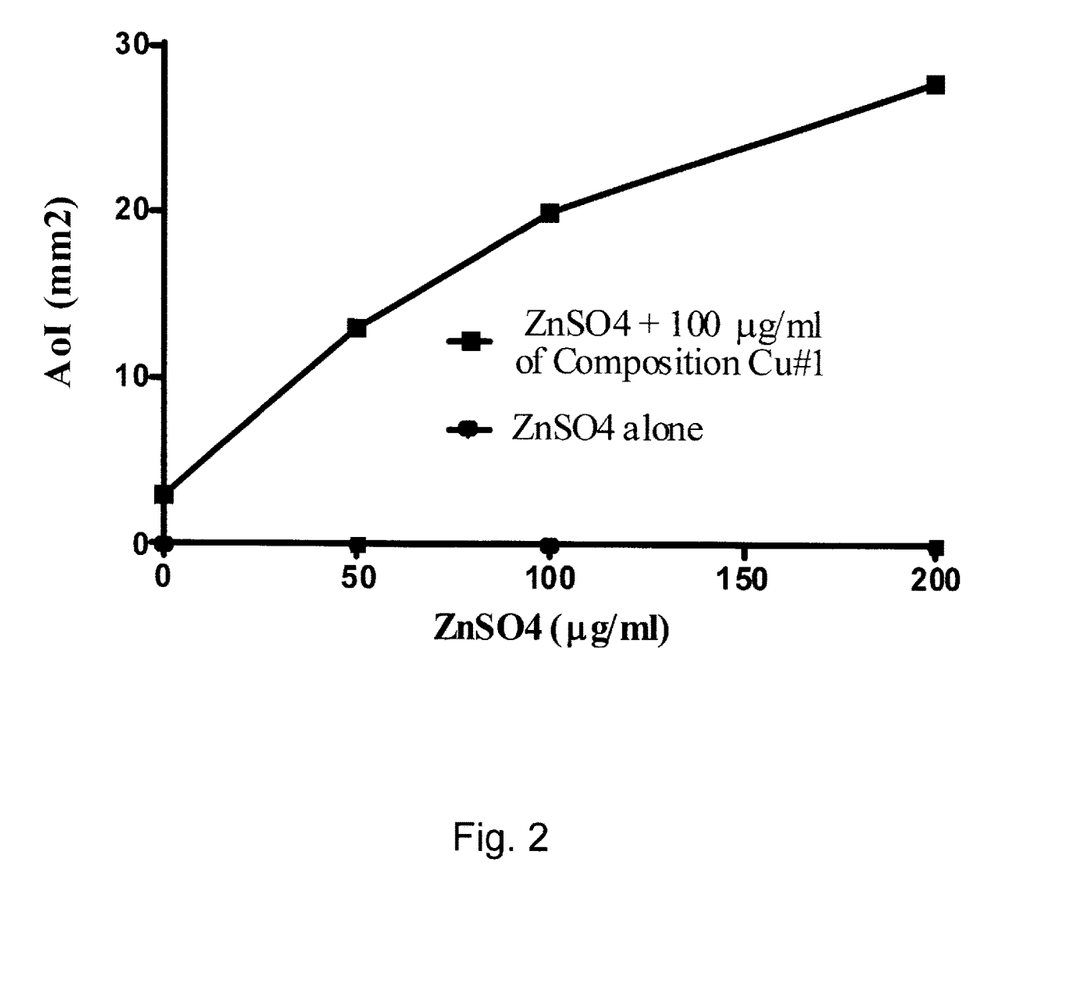
FIG. 2 is a graph depicting the effects of zinc sulfate alone and combined with composition Cu#1 on the growth of bacterial strain S1 (*S. aureus*)

2. The results in FIG. 2 compare the effects of zinc sulfate alone and combined with composition Cu#1 dissolved in gel on the growth of bacterial strain S1 (*S. aureus*) on TSA. Zinc sulfate alone had no effect on the growth of S1 (*S. aureus*) at any concentration tested (50-200 micrograms/milliliter). In contrast, when composition Cu#1 (100 micrograms/milliliter) was combined with increasing concentrations of zinc sulfate there was a clear synergistic inhibitory effect on the growth of S1 (*S. aureus*). Thus, composition Cu#1 alone had an AoI of 3 mm², but this increased to 13, 20 and 28 mm² when combined with zinc sulfate at concentrations of 50, 100 and 200 micrograms/milliliter, respectively. These results surprisingly show that antimicrobial acid-solubilized copper-ammonium complexes can act synergistically with zinc sulfate which alone has no antimicrobial activity against strain S1 (*S. aureus*). These results suggest that acid-solubilized copper-zinc-ammonium complexes may have advantageous antimicrobial activity against certain organisms.

Figure 3:
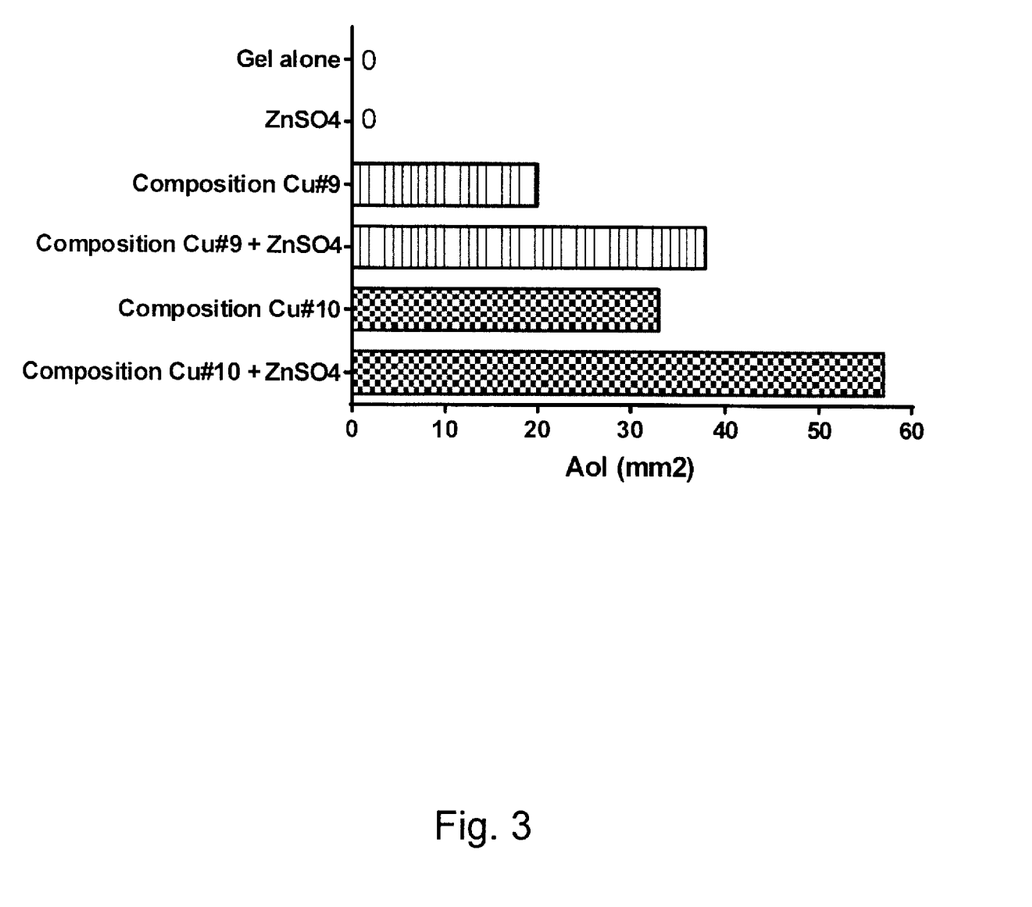
FIG. 3 is a bar chart depicting the effects of gel, zinc sulfate (100 μg/ml) alone and compositions Cu#9 or Cu#10 (200 μg/ml) alone and in combination with zinc sulfate on the growth of S1 (*S. aureus*)

3. FIG. 3 shows the effect of two compositions, Cu#9 and Cu#10 (200 micrograms/milliliter) in gel, alone and combined with zinc sulfate (100 micrograms/milliliter) in gel on the growth of S1 (*S. aureus*). The results show that the gel alone and zinc sulfate in gel have no effect on the growth of S1 (*S. aureus*). Compositions Cu#9 and Cu#10 in gel alone both inhibited the growth of S1 (*S. aureus*) with AoIs of 20 and 33 mm², respectively. In contrast, when combined with zinc sulfate in gel, compositions Cu#9 and Cu#10 showed increased inhibition of the growth of S1 (*S. aureus*) with AoIs of 38 and 57 mm², respectively. These results confirm and extend those shown in FIG. 2, demonstrating that there is a clear synergistic inhibitory effect on the growth of strain S1 (*S. aureus*) between acid-solubilized copper-ammonium complexes and zinc sulfate.

4. Table 3 shows the effect of copper sulfate, five different acid-solubilized copper-ammonium complexes and one acid-solubilized copper-zinc-ammonium complex on the growth of *P. acnes* on BHI agar as described in the methods section above. All of the acid-solubilized copper-ammonium complexes stock solutions were diluted 1:200 (vol/vol) and a copper sulfate solution of the same concentration of elemental copper (200 microgram/milliliter) was also prepared. The stock solution of composition Cu—Zn#1 (see Table 2 was also diluted 1:200 for testing. All dilutions were in distilled water.

TABLE 3

The effect of copper sulfate and various compositions (described in Tables 1 and 2) on the growth of *P. acnes* on BHI agar. There was no correlation between the antibacterial activity and the pH of the compositions.

| Composition | Zone of Inhibition (mm) | pH of stock solutions |
| --- | --- | --- |
| Copper sulfate | 13 | 3.4 |
| Cu#3 | 16 | 1.6 |
| Cu#9 | 16 | 2.2 |
| Cu#10 | 18 | 4.4 |
| Cu#12 | 19 | 2.0 |
| Cu#13 | 16 | 1.0 |
| Cu—Zn#1 | 18 | 1.5 |

The results in Table 3 show that all of the acid-solubilized copper-ammonium complexes were more inhibitory to the growth of *P. acnes* than an equivalent concentration of elemental copper in the form of copper sulfate. Although the ZoIs for the five Cu# compositions tested were similar, the formulations of the compositions were quite different—as shown in Table 1. Cu#3, Cu#9 and Cu#13 had the same ZoI but differed in the acid used to solubilize the copper-ammonium complex (phosphoric, hydrochloric and sulfuric acids, respectively) and Cu#13 comprises copper chloride rather than copper sulfate, Cu#12 (copper sulfate and sulfuric acid) had the greatest ZoI against *P. acnes* but differs only in the copper salt used in the composition from Cu#13 (see Table 1).

Since the copper-ammonium and copper-zinc-ammonium compositions are solubilized with acids it could be suggested that the acidity of the compositions is responsible for their greater antimicrobial activity when compared to copper sulfate. However, as shown in Table 3, the stock solution of Cu#10 has a higher pH than an equivalent solution of copper sulfate and yet has a greater inhibitory effect on the growth of *P. acnes*. Furthermore, a non-parametric Spearman correlation test between the ZoIs and pH's of the compound/compositions shown in Table 3 yielded a correlation coefficient=−0.056 with p=0.81 (using the Prism 6 (statistics package by GraphPad Software in La Jolla, Calif.), showing that there is no significant correlation between pH and antimicrobial activity for the compositions tested in this experiment.

Interestingly, composition Cu—Zn#1 was one of the more inhibitory compositions despite having only 37.5% of the elemental copper of the Cu# compositions, but in conjunction with an equimolar concentration of elemental zinc (1.5 grams/deciliter in the stock solution). The impressive activity of Cu—Zn#1 supports the conclusions from the results presented in FIGS. 2 and 3, that there is synergy between copper and zinc ions and shows that this acid-solubilized copper-zinc-ammonium complex demonstrates a greater than expected inhibitory effect against *P. acnes*. These results also suggest that composition Cu—Zn#1 may have therapeutic value in the treatment of acne, a disease strongly associated with *P. acnes*. Furthermore, since it is known that *P. acnes* does not grow well at pH 4.5-5, which is the pH range of "normal" skin, the acid-solubilized copper-zinc-ammonium complex Cu—Zn#1 may be of therapeutic value in the treatment of acne since it strongly inhibits the growth of *P. acnes* and the pH values of a 1% (vol/vol) formulation of Cu—Zn#1 in the gel with preservatives is around pH 4.6.

Example 2. Bacterial Microplate Cultures

The aerobic bacterial strains *Acinetobacter baumannii* (*A. baumannii*), methicillin-resistant *Staphylococcus aureus* (MRSA) and *Klebsiella pneumonia* (*K. pneumoniae*) were isolated from swabs taken in a hospital ward. *Escherichia coli* (NCTC 9001; *E. coli*) is a clinical isolate from a patient's urinary bladder; all strains were cultured in RPMI-1640. Stock solutions of the compounds/compositions to be tested were diluted so that double dilutions in the microplate assays commenced at a 1% vol/vol concentration. Double dilutions of the compositions to be tested were prepared in RPMI-1640 in a 96-well tissue culture plate. The bacterial cultures were diluted 1:40 with fresh RPMI and added to the compositions. *P. acnes* was cultured as described in EXAMPLE 1 (Agar plate test methods) and a sample was diluted 1:100 with fresh BHI. Double dilutions of the compositions to be tested were prepared as described above in distilled water in a 96-well tissue culture plate (100 microliters) and 100 microliters of the diluted *P. acnes* culture was added. The plates were then incubated at 37° C. for 24 hours (under anaerobic conditions for *P. acnes*). The minimum inhibitory concentration (MIC) of the compositions was defined as the lowest concentration at which no visible bacterial growth was observed.

Results

1. Table 4 shows the MIC results for copper sulfate, zinc sulfate and various compositions described in Tables 1 and 2. In Experiment #1, the two copper-based compositions tested (Cu#3 and Cu#9) were twice as active as copper sulfate. Surprisingly, zinc sulfate had a lower MIC with *P. acnes* than any of the Cu-based products and the acid-solubilized copper-zinc-ammonium formulation Cu—Zn#1 was the most active composition tested. Cu—Zn#3 which has the same amount of elemental copper as Cu—Zn#1 but 6-fold less elemental zinc (see Table 2) was 4-fold less active than Cu—Zn#1.

TABLE 4

The effect of copper sulfate and zinc sulfate and various compositions (described in Tables 1 and 2) on the growth of P. acnes in bacterial microplate cultures.

| Experiment #1 | | Experiment #2 | |
|---|---|---|---|
| Composition | MIC (µg/ml) | Composition | MIC (µg/ml) |
| Copper sulfate | 100 | Copper sulfate | 200 |
| Cu#3 | 50 | Cu#3 | 100 |
| Cu#9 | 50 | Cu#12 | 100 |
| Zinc sulfate | 25 | Cu#13 | 100 |
| Cu—Zn#1 | 12.5 | Cu—Zn#1 | 12.5 |
| Cu—Zn#3 | 50 | Cu—Zn#3 | 50 |

In Experiment #2, the MICs for copper sulfate and Cu#3 with P. acnes were double those seen in the first experiment but Cu#3 was still twice as active. Cu#12 and Cu#13 had the same MIC as Cu#3 despite comprising sulfuric acid rather than the phosphoric acid in Cu#3; Cu#13 comprised copper chloride rather than copper sulfate in Cu#3 and Cu#12. These results indicate that the acid-solubilized copper-ammonium complexes are generally more active than copper sulfate alone. As in Experiment #1, Cu—Zn#1 was the most active composition against the growth of P. acnes and was again 4-fold more active than Cu—Zn#3.

Overall these experiments confirm and extend the agar plate test results described above and shown in Table 3. The results confirm that acid-solubilized copper-ammonium compositions are more active than copper sulfate alone. The present results surprisingly showed that zinc sulfate inhibits the growth of P. acnes and that Cu—Zn#1 was considerably more active than any of the Cu# compositions, despite containing only 37.5% of the elemental copper. The results show that the combination of equimolar elemental zinc and copper in composition Cu—Zn#1 is the more active than zinc sulfate alone and even more active than Cu—Zn#3 which contains 6-fold less elemental zinc compared to copper. Overall the results of these experiments confirm that Cu—Zn#1 may have therapeutic benefit in acne.

2. Table 5 shows the MIC results for Cu—Zn compositions #1 to #5 which have varying ratios of elemental copper and zinc, whilst the amounts of ammonium carbonate used to make the Cu—Zn complexes and the amount of hydrochloric acid used to solubilize the Cu—Zn complexes remained constant (see Table 2). In this experiment, composition Cu#3 (used as a reference between experiments) had an MIC=50 micrograms/milliliter as did zinc sulfate. As in the previous experiments, composition Cu—Zn#1 was 4-fold more active against the growth of P. acnes than Cu—Zn#3 and in this experiment Cu—Zn#2, Cu—Zn#4 and #5 were both equally half as active as Cu—Zn#2 and #3 and 8-fold less active than Cu—Zn#1. These results show that composition Cu—Zn#1 comprising equimolar elemental copper and zinc is the most active composition against the growth of P. acnes of all those tested. The results with Cu—Zn#2 and #3 suggest that the role of copper against the growth of P. acnes is somewhat greater than that of zinc, but the surprising synergy of the two metals together when in equimolar equivalence (Cu—Zn#1) creates by far the most effective composition against the growth of P. acnes.

TABLE 5

The effect of various Cu—Zn# compositions, Cu#3 and zinc sulfate on the growth of P. acnes in bacterial microplate cultures.

| Composition | Ratio of elemental Cu:Zn | MIC (µg/ml) |
|---|---|---|
| Cu#3 | — | 50 |
| Zinc sulfate | — | 50 |
| Cu—Zn#1 | 1:1 | 6.3 |
| Cu—Zn#2 | 1:0.33 | 25 |
| Cu—Zn#3 | 1:0.17 | 25 |
| Cu—Zn#4 | 0.33:1 | 50 |
| Cu—Zn#5 | 0.17:1 | 50 |

3. Table 6 shows the MIC results for copper sulfate and various Cu# and Cu—Zn# compositions against the growth of MRSA, P. coli, A. baumannii and K. pneumoniae in microplate cultures. MRSA and A. baumannii are both clearly more sensitive to the effects of the copper sulfate, Cu# and Cu—Zn# compositions than E. coli and K. pneumonia, with A. baumannii being surprisingly sensitive to the inhibitory effect of the Cu—Zn# compositions. Since A. baumannii is a particularly persistent bacterium that causes healthcare acquired infections (HAIs), cleaning and/or fogging with composition Cu—Zn#1 may be particularly useful in freeing hospitals and other healthcare facilities from this increasingly prevalent and difficult to treat microbe.

TABLE 6

The effect of copper sulfate and various Cu# and Cu—Zn# compositions (described in Tables 1 and 2) on the growth of MRSA, E. coli, A. baumannii and K. pneumoniae in bacterial microplate cultures. NT = Not tested.

| Composition | MRSA | E. coli | A. baumannii | K. pneumoniae |
|---|---|---|---|---|
| Copper sulfate | 12.5 | 100 | 6.3 | 50 |
| Cu#3 | 6.3 | 50 | 3.1 | 12.5 |
| Cu#9 | 6.3 | 50 | 3.1 | 25 |
| Cu#10 | 6.3 | 100 | 3.1 | 25 |
| Cu#12 | 6.3 | 50 | 1.6 | 25 |
| Cu#13 | 6.3 | 100 | 3.1 | 25 |
| Cu—Zn#1 | 25 | 200 | 0.31 | 3.1 |
| Cu—Zn#3 | 25 | 200 | 0.63 | 6.3 |
| Cu#3a | 6.3 | 50 | 1.6 | NT |
| Cu10a | 6.3 | 50 | 1.6 | NT |
| Cu#11a | 6.3 | 50 | 1.6 | NT |

MRSA and E. coli were both more sensitive to the growth inhibitory effects of the Cu# compositions than the Cu—Zn# compositions and copper sulfate, whilst the opposite was true for A. baumannii and K. pneumoniae. However, E. coli was generally around 8-fold less sensitive to all of the compositions tested than MRSA.

It was noted that certain compositions made with ammonium carbonate or ammonium hydrogen carbonate and using acetic acid (Cu#10) and citric acid (Cu#11; not shown in Table 1 or tested because precipitation was noticeable after 24 hr), started to precipitate within days of preparation. Very similar compositions were made using ammonium hydroxide and these compositions (Cu#10a and Cu#11a) proved to be surprisingly more stable and showed no signs of precipitation after months of preparation (storage at room temperature). Three compositions were made using ammonium hydroxide (see Table 1 for details) and tested against MRSA, A. baumannii and E. coli as shown at the bottom of Table 6. Cu#3 is a stable composition and Cu#3a was equally as stable and active against the three bacterial strains tested. Cu10a showed similar activity to Cu#10 and Cu#11a with citric acid was as active as the other Cu#compositions. Not only are these (and other compositions prepared with ammonium hydroxide—see below) compositions more stable, they are quicker and easier to make because no carbon dioxide is liberated, and the Cu—/Cu—Zn-ammonium complexes formed with ammonium hydroxide require less acid for solubilization, so the pH of the compositions can be higher, representing advantages in formulations thereof.

MRSA is perhaps the best known and most problematic pathogenic bacterium causing HAIs, but the USA300 MRSA strain has also become an increasing concern in community-associated infections particularly of the skin. Carbapenem-resistant *K. pneumoniae* (CRKP) has emerged over the past 10 years to become a worldwide nosocomial pathogen that is almost totally drug-resistant. However, the sensitivity of the bacterial strains tested to Cu# and Cu—Zn# compositions Table 6), suggests that these compositions may be useful for cleaning, fogging and the like in hospitals, homes and other buildings to remove these organisms. Overall, since *A. baumannii* is also rather sensitive to the Cu# compositions, Cu#3 may be a particularly effective composition for cleaning and disinfection to remove these pathogenic microbes from buildings.

Example 3. Cytotoxicity Assay with a Human Squamous Epithelial Skin Cell Line (A-431)

Figure 4:
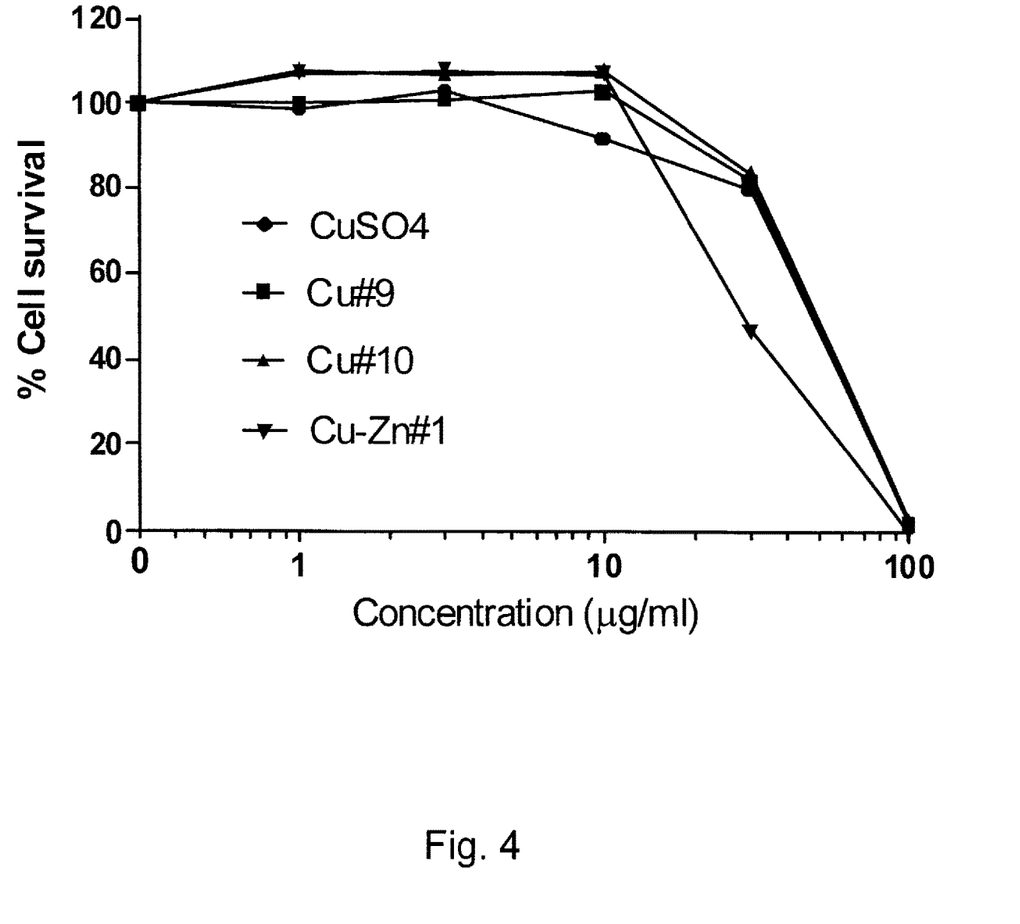
FIG. 4 is a graph of human skin cell survival after a 24 hour culture with copper sulfate and compositions Cu#9, Cu#10 and Cu—Zn#1: Gel+Cu#9, Gel+Cu—Zn#1.
Figure 5:
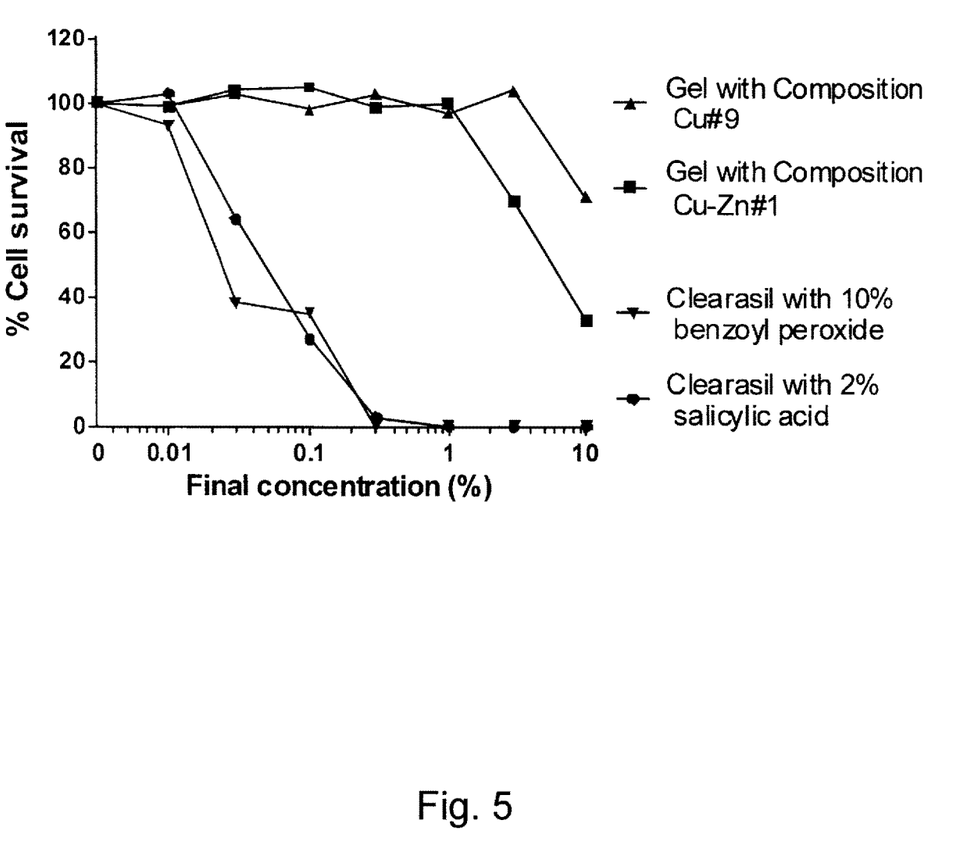
FIG. 5 is a graph of human skin cell survival after a 24 hour culture with Gel+Cu#9, Gel+Cu—Zn#1, and two CLEARASIL® (a trademark of Reckitt Benckiser LLC of Berkshire, England) anti-acne cream products containing the active compounds salicylic acid and benzoyl peroxide.

A-431 (ATCC) was cultured in RPMI-1640 medium supplemented with 10% fetal bovine serum and 2 mM L-glutamine (complete medium) in a humidified incubator at 37° C. with a 5% $CO_2$ in air atmosphere. For cytotoxicity experiments the cells were trypsinized, washed, counted and $2\times10^4$ cells were plated into the wells of flat-bottom 96-well plates in complete medium and cultured for 3 days until a confluent monolayer was formed. The products tested were: (i) Copper sulfate, Cu#9, Cu#10 and Cu—Zn#1 as shown in FIG. 4, and (ii) compositions Cu#9 and Cu—Zn#1 diluted in the Aloe vera gel with preservatives along with two commercial acne creams: CLEARASIL® (a registered trademark of Reckitt Benckiser LLC of Berkshire England) ultra rapid action treatment gel with 2% salicylic acid and CLEARASIL® (a registered trademark of Reckitt Benckiser LLC of Berkshire England) daily clear acne treatment cream with 10% benzoyl peroxide as shown in FIG. 5. All test products were diluted in complete medium and then added in triplicate to the confluent A-431 cells which were then cultured for a further 24 hours when cytotoxicity/cell survival was quantitatively assessed using the sulforhodamine B (SRB) assay as described below.

The cells were washed twice with RPMI1640 medium and then fixed with 10% trichloroacetic acid for 1 hour at 4° C. After washing twice with tap water, the cells were stained with SRB (0.4% w/v SRB acetic acid) for 30 min at room temperature. After washing twice with tap water the remaining stain was dissolved in 10 mM Tris base and the absorbance of the wells was measured on a Dynatech Multiplate ELISA reader at 540 nm. Percent cell survival was calculated by dividing the test product absorbance by control absorbance and multiplying by 100.

Results

FIG. 4 shows that copper sulfate and compositions Cu#9 and 10 had almost identical cytotoxicity profiles with human skin cells with 50% cytotoxic concentrations ($CC_{50}$) of 50 micrograms/milliliter, suggesting that copper ions are responsible for the cytotoxic effects of the three products. The composition Cu—Zn#1 was slightly more cytotoxic than the other three products ($CC_{50}$=30 micrograms/milliliter), presumably owing to the presence of both copper and zinc ions, albeit with the elemental copper concentrations being only 37.5% of the other three products, suggesting that zinc ions are even more cytotoxic than copper ions to human skin cells and/or they enhance the cytotoxicity of copper ions.

Importantly, these results show that compositions described herein such as Cu#3, #3a, #9, #10, #10a, #11a, #12, #13 and Cu—Zn#1 and #3 can inhibit the growth of bacteria such as MRSA and *A. baumannii* at concentrations (MIC 1.6-6.3 microgram/milliliter—see Table 6) well below those that cause cytotoxicity to human skin cells in culture (around 30 micrograms/milliliter). Cu—Zn#1 also inhibits the growth of *P. acnes* with an MIC=12.5 micrograms/millilitre (Table 4) at which concentration it is not cytotoxic to human skin cells.

FIG. 5 shows the effects of gel containing 1% vol/vol of compositions Cu#9 (400 micrograms/milliliter elemental copper) and Cu—Zn#1 (150 micrograms/liter elemental copper and zinc) and two commercially available CLEARASIL® (a registered trademark of Reckitt Benckiser LLC of Berkshire England) acne creams on the survival of human skin cells in tissue culture. Both of the CLEARASIL® (a registered trademark of Reckitt Benckiser LLC of Berkshire England) products, one containing 10% benzoyl peroxide and the other containing 2% salicylic acid as active ingredients, produced similar cytotoxicity profiles with $CC_{50}$ values of 0.02% and 0.05%, respectively, and 100% cytotoxicity (0% cell survival) at concentrations around 0.5% and above. Gel containing 1% of composition Cu—Zn#1, which would be the preferred composition for treating acne, had a $CC_{50}$ of 4%, while the gel containing 1% of composition Cu#9 did not achieve a $CC_{50}$ even at 10% vol/vol in the assay. These gel formulation $CC_{50}$ values are compatible with the $CC_{50}$ values obtained with the compositions alone (see FIG. 4) Therefore, it is clear that the CLEARASIL® (a registered trademark of Reckitt Benckiser LLC of Berkshire England) products are around 200-fold more toxic to human skin cells than either of the gel formulations.

It is important to note that owing to the relative simplicity of skin cell cultures compared to the complex structure of skin, the healthcare implications need to be interpreted with care and these in vitro results may not translate into clinical differences. Nevertheless, it appears that the active ingredients in the CLEARASIL® (a registered trademark of Reckitt Benckiser LLC of Berkshire England) products, salicylic acid and benzoyl peroxide, which are widely used in acne treatment products, are particularly toxic to skin cells which may be more exposed on the skin of people suffering from acne. Thus the gel with the Cu—Zn#1 formulation may be less damaging to the skin of acne sufferers, whilst being highly active against the *P. acnes*, the bacterium associated with acne (see EXAMPLES 1 and 2).

Example 4. Anti-Fungal Assays with Plant Pathogenic Fungi

*Chalara fraxinea* isolate 196/28 (*C. fraxinea*), *Aspergillus niger* (*A. niger*) and a strain isolated from powdery mildew (Pm; isolated from an apple leaf) were cultured on potato dextrose agar (PDA) at room temperature (around 22° C.). To assess the effects of compositions on fungal growth, 10 microliters of the test compositions diluted in sterile distilled water were placed in the wells of a 12-well tissue culture plate and 1 milliliter of PDA was added by pipette to each well. The plate was agitated to evenly distribute the test composition evenly through the agar (distilled water alone was used as control) and then the agar was allowed to set. Plugs of agar containing fungal hyphae (3 mm²) from an established fungal culture were carefully cut out using a scalpel and inserted into holes in the centre of the agar in each well of the 12-well plate which was then cultured at room temperature (around 22° C.). Since the rate of fungal growth varies depending on the strain, the experiments were assessed after 3 days for Pm, and at appropriate intervals of 3-4 days for *A. niger* and around 7 days for *C. fraxinea*. To assess the effects of compositions on fungal growth, the diameter of the fungal hyphae was measured twice at a 90° angle using a ruler and the average diameter in millimeters was calculated. If no fungal growth could be detected by eye, the cultures were observed by phase microscopy (40×) to confirm that there was no growth (NG) as judged by visual examination.

Results

1. Table 7 shows the effects of copper sulfate and composition Cu#16 on the growth of *C. fraxinea*. Composition Cu#16 strongly inhibited fungal growth at a concentration of 125 micrograms/milliliter at both time points and was around 30-times more inhibitory to fungal growth than copper sulfate (results with 3.75 micrograms/milliliter Cu#16 were very similar to those with 125 micrograms/milliliter of copper sulfate), presumably owing to the solubilization of the copper-ammonium complex in Cu#16 with phosphorous acid (see Table 1), which is known to have anti-fungal activity.

TABLE 7

The effects of copper sulfate and composition Cu#16 on the growth of *C. fraxinea* on PDA. *Slight growth observed by phase microscopy at 40X magnification. **20 millimeters is the width of the wells and represents confluent fungal growth.

|  | Diameter of fungal growth (mm) | |
| --- | --- | --- |
|  | Day 7 | Day 15 |
| CuSO$_4$ (µg/ml) | | |
| 125 | 10 | 18 |
| 37.5 | 13 | 20** |
| 12.5 | 14 | 20 |
| 3.75 | 14 | 20 |
| Cu#16 (µg/ml) | | |
| 125 | 3* | 4 |
| 37.5 | 7 | 10 |
| 12.5 | 9 | 15 |
| 3.75 | 10 | 17 |
| Control | 14 | 20 |

2. Table 8 shows the effects of compositions Cu—Zn#1 and Cu—Zn#7 on the growth of *C. fraxinea*. Composition Cu—Zn#1 is less effective than composition Cu—Zn#7 at inhibiting the growth of *C. fraxinea* and although the formulations of the two compositions are very similar (Table 2), composition Cu—Zn#7 contains phosphorous acid as the copper-zinc solubilizing acid whereas Cu—Zn#1 contains hydrochloric acid. Phosphorous acid is known to have anti-fungal activity and its use in composition Cu—Zn#7 results in an anti-fungal composition that is 3- to 10-fold more active than Cu—Zn#1 on days 7 and 14 of the assay, respectively.

A 1% concentration of Cu—Zn#7 contains 150 micrograms/millilitre of elemental copper, so comparing the effects of Cu—Zn#7 to those of copper sulfate and Cu#16 in Table 7 indicates that Cu—Zn#7 is a slightly less effective inhibitor of *C. fraxinea* growth than Cu#16, but it is considerably more effective than copper sulfate.

TABLE 8

The effect of compositions Cu—Zn#1 and Cu—Zn#7 on the growth of *C. fraxinea* on PDA. The Cu—Zn# compositions were used as a percent dilution of the stock solutions (Table 2), so a 1% solution contains 150 µg/ml of elemental copper (and zinc). *20 millimeters is the width of the wells and represents confluent fungal growth.

|  | Diameter of fungal growth (mm) | |
| --- | --- | --- |
|  | Day 7 | Day 14 |
| Cu—Zn#1 (%) | | |
| 1 | 7 | 18 |
| 0.3 | 16 | 20* |
| 0.1 | 16 | 20 |
| 0.03 | 16 | 20 |
| 0.01 | 16 | 20 |
| Cu—Zn#7 (%) | | |
| 1 | 4 | 8 |
| 0.3 | 8 | 14 |
| 0.1 | 15 | 17 |
| 0.03 | 16 | 19 |
| 0.01 | 16 | 20 |
| Control | 16 | 20 |

3. Table 9 shows the effects of copper sulfate and composition Cu#16 on the growth of *A. niger*. Composition Cu#16 completely inhibited fungal growth at a concentration of 125 micrograms/milliliter and at all three time points was 3- to 10-fold more inhibitory to fungal growth than copper sulfate as was seen with *C. fraxinea* (Table 7).

TABLE 9

The effects of copper sulfate and composition Cu#16 on the growth of *A. niger* on PDA. NG indicates no growth as assessed by phase microscopy at 40X magnification.

|  | Diameter of fungal growth (mm) | | |
| --- | --- | --- | --- |
|  | Day 4 | Day 7 | Day 11 |
| CuSO$_4$ (µg/ml) | | | |
| 125 | 7 | 10 | 15 |
| 37.5 | 13 | 16 | 18 |
| 12.5 | 15 | 17 | 18 |
| Cu#16 (µg/ml) | | | |
| 125 | NG | NG | NG |
| 37.5 | 8 | 11 | 12 |
| 12.5 | 11 | 14 | 14 |
| Control | 15 | 17 | 18 |

4. Table 10 shows that both Cu# compositions which both contain phosphorous acid were more effective than copper sulfate at inhibiting the growth of Pm. Composition Cu#16 was made with ammonium hydrogen carbonate whilst Cu#27 contains ammonium hydroxide and as shown before (Table 6), this made no significant difference to the anti-fungal activity of the composition. However, precipitation was noted in composition Cu#16 after a few days at room temperature whilst this was not seen with Cu#27, suggesting that ammonium hydroxide may be surprisingly advantageous in the preparation of copper-ammonium complexes when phosphorous acid is used to solubilize the complex. Compositions Cu—Zn#7 and Cu—Zn#10, which were equally effective inhibitors of Pm growth, differed in the use of ammonium carbonate and ammonium hydroxide, respectively, to create the Cu—Zn-ammonium complexes which were solubilized with phosphorous acid in each case (Table 2). However, no precipitation was noted when ammonium carbonate was used to prepare Cu—Zn-ammonium complexes that were solubilized with phosphorous acid. Surprisingly, the Cu—Zn# compositions were more effective inhibitors of Pm growth than the Cu# compositions in terms of elemental copper content. Thus, at a 1 percent dilution (150 micrograms/millilitre of copper) the Cu—Zn# compositions completely inhibited growth as did the Cu# compositions but at 375 micrograms/millilitre of elemental copper. At a 0.3 percent dilution (45 micrograms/millilitre of copper) the Cu—Zn# compositions still strongly inhibited Pm growth, whilst at 37.5 micrograms/millilitre the Cu# compositions were only slightly inhibitory to Pm growth. Calculations indicate that the concentration required to inhibit the growth of Pm by 50% was around 40 micrograms/milliliter for the Cu—Zn# compositions and around 170 micrograms/milliliter for the Cu# compositions. Therefore, these results show that the Cu—Zn# compositions solubilized with phosphorous acid are surprisingly more effective than the Cu# compositions solubilized with phosphorous acid at inhibiting the growth of Pm, regardless of the ammonium salt used to form the complexes.

TABLE 10

The effects of copper sulfate, two Cu# compositions and two Cu—Zn# compositions on the growth of Pm on PDA after 3 days of culture. The Cu—Zn# compositions were used as a percent dilution of the stock solutions (Table 2), so a 1% solution contains 150 μg/ml of elemental copper (and zinc). NG indicates no growth as assessed by phase microscopy at 40X magnification. *Slight growth observed by phase microscopy at 40X magnification.

| Composition | Diameter of fungal growth (mm) | | | |
|---|---|---|---|---|
| | 12.5 μg/ml | 37.5 μg/ml | 125 μg/ml | 375 μg/ml |
| CuSO$_4$ | 17 | 17 | 13 | 3* |
| Cu#16 | 17 | 15 | 10 | NG |
| Cu#27 | 17 | 16 | 10 | NG |
| | 0.03% | 0.1% | 0.3% | 1% |
| Cu—Zn#7 | 17 | 14 | 4 | NG |
| Cu—Zn#10 | 17 | 14 | 3* | NG |
| Control | | 17 | | |

*C. fraxinea* is the cause of ash tree die-back which is a serious forestry problem in Europe. *A. niger* causes black mold on certain fruits and vegetables such as grapes, onions, and peanuts, and is a common contaminant of food. Fungi of the Genus *Blumeria* are widespread plant pathogens that cause powdery mildew on the leaves of many plants including grapevines, Curcubits, onions, apple and pear trees. The results described above show that copper-ammonium and copper-zinc-ammonium complexes solubilized with phosphorous acid are highly effective at inhibiting the growth of the various plant pathogenic fungi tested and therefore may have practical applications in the agricultural field for protecting of crops, plants, trees, flowers and ornamental shrubs. Surprisingly, Cu—Zn#7 and #10 were significantly more effective than Cu#16 and #27 at inhibiting the growth of Powdery mildew suggesting these compositions may have advantageous anti-fungal activity against certain plant pathogens.

Example 5. Anti-Fungal/Yeast Assays with the Human Pathogens *Candida albicans* and *Cryptococcus neoformans*

The three strains of *Candida albicans* (*C. albicans*) used: 1-1, 3-1 and 4-1 were isolated from human blood, vagina and oropharynx, respectively. *Cryptococcus neoformans* (*C. neoformans*) strain CCTP13 was used. All strains were cultured in RPMI-1640 medium at 37° C. The copper sulfate and Cu# compositions started at a high concentration of 200 micrograms/millilitre, whilst the Cu—Zn# compositions started at a high concentrations of 1% of the stock solution (Table 2) and zinc sulfate and phosphorous acid started with a high concentrations equivalent to those in Cu—Zn#7 and #10 (see the legend of Table 11 for details) doubling dilutions (100 microliters) of the compositions were prepared in RPMI-1640 in a 96-well tissue culture plate. Overnight *C. albicans* and *C. neoformans* cultures were diluted 1:40 and 1:10 respectively with fresh RPMI containing 40 mM MOPS buffer and 90 microliters was added to the compositions in the plate. Resazurin A (10 microliters of a 0.0675% wt/vol solution in distilled water) was added as an indicator of growth, and the cultures were incubated at 37° C. for 24 hr. The minimum inhibitory concentration (MIC) of the compounds/compositions was defined as the lowest concentration at which the resazurin A indicator remained blue (living cells convert the blue dye to a pink color).

Results

Table 11 shows that all of the strains tested were surprisingly sensitive to copper, with MICs similar to those seen with MRSA and *A. baumannii* (around 6 micrograms/milliliter; Table 6), whether in the form of copper sulfate or the acid-solubilized copper-ammonium compositions (Cu#).

The acid-solubilized Cu—Zn-ammonium complex compositions #1 and #7 which contain equimolar amounts of elemental copper and zinc with hydrochloric and phosphorous acids, respectively, were slightly more effective inhibitors of *C. albicans* growth than copper sulfate and the Cu# compositions in terms of copper ion concentration (MIC=4.7 micrograms/milliliter of elemental $Cu^{2+}$). The yeast *C. neoformans* was also highly sensitive to copper regardless of the form, but was less sensitive to Cu—Zn#1 than the *C. albicans* strains. The growth of the *C. albicans* strains was not affected by zinc sulfate or phosphorous acid (MIC>150 and >500 micrograms/millilitre, respectively). The growth of *C. neoformans* was also unaffected by zinc sulfate.

TABLE 11

The effect of various compositions on the growth of three *C. albicans* strains and a strain of *C. neoformans*. *The Cu—Zn# compositions contain 4.7 μg/ml of both $Cu^{2+}$ and $Zn^{2+}$.
**A 1% vol/vol solution of the Cu—Zn#7 and #10 stock compositions (see Table 2) contains 150 μg/ml of zinc sulfate and 500 μg/ml of phosphorous acid. NT = not tested.

| | MIC (μg/ml $Cu^{2+}$) | | | |
|---|---|---|---|---|
| Composition | 1-1 | 3-1 | 4-1 | C. neoformans |
| CuSO$_4$ | 6.3 | 6.3 | 6.3 | 6.3 |
| Cu#3 | 6.3 | 6.3 | 6.3 | 6.3 |
| Cu#9 | 6.3 | 6.3 | 6.3 | 6.3 |
| Cu#12 | 6.3 | 6.3 | 6.3 | 6.3 |
| Cu#16 | 6.3 | 6.3 | 6.3 | NT |
| Cu—Zn#1 | 4.7* | 4.7 | 4.7 | 18.8 |
| Cu—Zn#7 | 4.7 | 4.7 | 4.7 | NT |

TABLE 11-continued

The effect of various compositions on the growth of three *C. albicans* strains and a strain of *C. neoformans*. *The Cu—Zn# compositions contain 4.7 µg/ml of both $Cu^{2+}$ and $Zn^{2+}$.
**A 1% vol/vol solution of the Cu—Zn#7 and #10 stock compositions (see Table 2) contains 150 µg/ml of zinc sulfate and 500 µg/ml of phosphorous acid. NT = not tested.

| Composition | MIC (µg/ml $Cu^{2+}$) | | | |
|---|---|---|---|---|
| | 1-1 | 3-1 | 4-1 | *C. neoformans* |
| $ZnSO_4$ | >150 | >150 | >150 | >150 |
| $H_3PO_3$ | >500 | >500 | >500 | NT |

These results show that *C. albicans* strains isolated from a variety of different anatomical sites are all highly sensitive to the presence of copper when grown in RPMI medium. Thus, it may be concluded that either of the Cu# or Cu—Zn# compositions may be useful in the topical treatment of *C. albicans*-related diseases such as vaginal and oral thrush.

*C. neoformans* was also very sensitive to copper sulfate and the Cu# compositions, but was much less sensitive to Cu—Zn#1 and zinc sulfate. *C. neoformans* causes severe meningitis in people with HIV/AIDS and selective delivery of a copper-containing complex to the brain may be a potential therapy for this lethal disease.

Example 6. Stability Tests

Samples (3 milliliters) of composition Cu#1 and Aloe vera gel with preservatives containing 1% vol/vol of composition Cu#1 were placed in 7 milliliter sterile plastic tubes and replicate samples were stored under four conditions; at 37° C. in a humidified incubator, at room temperature (around 22° C.) in a cupboard, at 4° C. in a cold room, and at −20° C. in a freezer. After 5 months of storage, a set of samples of Cu#1 and the gel containing 1% Cu#1 were allowed to come to room temperature. The gel samples (5 microliters) and the samples of Cu#1 (diluted 1:1 or 1:10 vol/vol in distilled water and 5 microliters placed on a paper disc) were tested against bacterial strain S1 (*S. aureus*) in the agar plate test, and after 24 hour culture at 37° C., the diameters of the zones of inhibition were measured as described in EXAMPLE 1.

Results

The samples of the gel containing 1% of composition Cu#1 all gave zones of inhibition of 6 millimeters against S1 (*S. aureus*), indicating that storage at a wide range of temperatures had no effect on the anti-bacterial activity of the gels.

Table 12 shows the zones of inhibition for the samples of composition Cu#1 stored at various temperatures for 5 months. The sample stored at 37° C. was slightly more inhibitory to the growth of S1 (*S. aureus*) than the other samples which gave very similar zones of inhibition at both concentrations tested. These results show that composition Cu#1 retains its antibacterial activity after 5 months of storage at a wide range of temperatures.

TABLE 12

The effect of samples of composition Cu#1 stored at various temperatures for 5 months on the growth of bacterial strain S1 (*S. aureus*) in the agar plate test.

| | Zone of inhibition (mm) | |
|---|---|---|
| Cu#1 storage temperature | 1:1 dilution | 1:10 dilution |
| 37° C. | 23 | 12 |
| Room temperature (~22° C.) | 19 | 10 |
| 4° C. | 20 | 9 |
| −20° C. | 18 | 8 |

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims and the attached drawings.

What is claimed is:

1. An antimicrobial composition produced by the process of: combining 10-160 grams/liter of hydrated copper sulfate with water; stirring the combined mixture and adding 20-32 milliliters/liter of an ammonium hydroxide solution to the resulting mixture to generate an insoluble copper-ammonium complex; and adding a water soluble acid selected from the group consisting of phosphorous acid and phosphoric acid to the copper-ammonium complex to solubilize the copper-ammonium complex and to control the pH of the clear blue solution thus formed; wherein the concentration of elemental copper in the clear blue solution is between 15 and 40 grams/liter, wherein when present the amount of phosphorous acid is 24-50 grams/liter and wherein when present the amount of phosphoric acid is 17-85 grams/liter, the resulting composition having synergistic antimicrobial properties greater than the antimicrobial properties of each constituent component.

2. The antimicrobial composition of claim 1, wherein the water is selected from the group consisting of distilled water, deionized water, purified water, filtered water, pharmaceutical grade water, medical grade water, and reverse osmosis water.

3. The antimicrobial composition of claim 1 wherein the hydrated copper sulfate solution further comprises 2.5-15 grams/liter of elemental zinc from a zinc salt in solution forming a copper-zinc-ammonium complex upon the addition of the ammonium hydroxide solution.

4. The antimicrobial composition of claim 3, wherein the zinc salt is selected from the group consisting of anhydrous or hydrated zinc sulfate.

5. The antimicrobial composition of claim 1, further comprising auxiliaries, adjuvants, carriers, surfactants, coating agents or extenders.

6. The antimicrobial composition of claim 1, further comprising a carrier selected from the group consisting of a gel, an ointment, an oil, a paste, a medicament, a sprayable solution, a dressing solution, an irrigation solution, a cream, a soap, a detergent, a wash, and a foam.

7. A method of producing an antimicrobial composition comprising the steps of: combining 10-160 grams/liter of hydrated copper sulfate with water; stirring the combined hydrated copper sulfate and water mixture; adding 20-32 milliliters/liter of ammonium hydroxide solution to the resulting mixture to generate an insoluble copper-ammonium complex; and adding a water soluble acid selected from the group consisting of phosphorous acid and phosphoric acid to the copper-ammonium complex to solubilize the copper-ammonium complex and to control the pH of the clear blue antimicrobial composition thus formed; wherein the concentration of elemental copper in the clear blue solution is between 15 and 40 grams/liter, wherein when present the amount of phosphorous acid is 24-50 grams/liter and wherein when present the amount of phosphoric acid is 17-85 grams/liter; the resulting composition having synergistic antimicrobial properties greater than the antimicrobial properties of each constituent component.

8. A method comprising applying to at least one of a living organism or an environment communicable therewith an effective amount of a liquid including a diluted solution of an anti-microbial composition comprising an acid-solubilized metal-ammonium complex and a water soluble acid added thereto; the water soluble acid selected from the group consisting of phosphorous acid and phosphoric acid, and added to the copper-ammonium complex to solubilize the copper-ammonium complex and to control the pH of the clear blue solution thus formed; wherein the metal-ammonium complex is selected from copper-ammonium complex, zinc ammonium complex, and combinations of copper-ammonium and zinc-ammonium complex, wherein when present the concentration of elemental copper in the diluted solution is between 0.15 and 0.4 grams/liter, wherein when present the concentration of elemental zinc in the diluted solution is between 0.025 and 0.15 grams/liter, wherein when present the amount of phosphorous acid is 0.24 and 0.5 grams/liter and wherein when present the amount of phosphoric acid is between 0.17 and 0.85 grams/liter, the resulting composition having synergistic antimicrobial properties greater than the antimicrobial properties of each constituent component.

9. The method of claim 8, wherein the metal-ammonium complex is copper-ammonium complex.

10. The method of claim 8, wherein the metal-ammonium complex is zinc-ammonium complex.

11. The method of claim 8, wherein the metal-ammonium complex is copper-zinc-ammonium complex.

12. The method of claim 8, wherein the living organism is a plant, and the method comprises applying the antimicrobial composition as a spray to at least one of a seed, flower, foliage, or environment of the plant.

13. The method of claim 8, wherein the living organism includes skin tissue, and the skin tissue or the environment communicable therewith.

14. An antimicrobial soluble copper composition comprising: a solution comprising 10-160 grams/liter hydrated copper sulfate; ammonium hydroxide added to the hydrated copper sulfate solution at 20-32 milliliters/liter to generate an insoluble copper-ammonium complex; and at least one water soluble acid selected from the group consisting of phosphorous acid and phosphoric acid added to the hydrated copper sulfate solution to solubilize the copper-ammonium complex and to control the pH of the clear blue acid-solubilized copper-ammonium solution thus formed; wherein the concentration of elemental copper in the clear blue solution is between 15 and 40 grams/liter, wherein when present the amount of phosphorous acid is 24-50 grams/liter and wherein when present the amount of phosphoric acid is 17-85 grams/liter; the resulting composition having synergistic antimicrobial properties greater than the antimicrobial properties of each constituent component.

15. The antimicrobial composition of claim 14, wherein the water is selected from the group consisting of distilled water, deionized water, purified water, filtered water, pharmaceutical grade water, medical grade water, and reverse osmosis water.

16. The antimicrobial composition of claim 14, wherein the hydrated copper sulfate solution further comprises 2.5-15 grams/liter of elemental zinc from a zinc salt in solution forming a copper-zinc-ammonium complex upon the addition of the ammonium hydroxide solution.

17. The antimicrobial composition of claim 16, wherein the zinc salt is selected from the group consisting of anhydrous or hydrated zinc sulfate.

18. The antimicrobial composition of claim 14, further comprising auxiliaries, adjuvants, carriers, surfactants, coating agents or extenders.

19. The antimicrobial composition of claim 14, further comprising a carrier selected from the group consisting of a gel, an ointment, an oil, a paste, a medicament, a sprayable solution, a dressing solution, an irrigation solution, a cream, a soap, a detergent, a wash, and a foam.

* * * * *